United States Patent
Chase et al.

(10) Patent No.: US 11,318,122 B2
(45) Date of Patent: May 3, 2022

(54) PHARMACEUTICAL COMBINATION AND ITS USE FOR TREATING SYNUCLEINOPATHTIES

(71) Applicant: CHASE THERAPEUTICS CORPORATION, Washington, DC (US)

(72) Inventors: Thomas N. Chase, Washington, DC (US); Kathleen E. Clarence-Smith, Washington, DC (US)

(73) Assignee: CHASE THERAPEUTICS CORPORATION, Washington, DC (US)

( * ) Notice: Subject to any disclaimer, the term of this patent is extended or adjusted under 35 U.S.C. 154(b) by 22 days.

(21) Appl. No.: 16/604,689

(22) PCT Filed: Apr. 11, 2018

(86) PCT No.: PCT/US2018/027155
§ 371 (c)(1),
(2) Date: Oct. 11, 2019

(87) PCT Pub. No.: WO2018/191408
PCT Pub. Date: Oct. 18, 2018

(65) Prior Publication Data
US 2020/0375956 A1    Dec. 3, 2020

Related U.S. Application Data

(60) Provisional application No. 62/485,082, filed on Apr. 13, 2017.

(51) Int. Cl.
*A61P 25/16* (2006.01)
*A61K 31/428* (2006.01)
*A61K 31/138* (2006.01)

(52) U.S. Cl.
CPC .......... *A61K 31/428* (2013.01); *A61K 31/138* (2013.01); *A61P 25/16* (2018.01)

(58) Field of Classification Search
CPC ...................................................... A61P 25/16
See application file for complete search history.

(56) References Cited

U.S. PATENT DOCUMENTS

| 5,910,319 A | 6/1999 | Anderson et al. |
| 6,667,329 B1 * | 12/2003 | Maj ...................... A61K 31/425 |
| | | 514/367 |
| 2013/0230569 A1 | 9/2013 | Bozik et al. |

FOREIGN PATENT DOCUMENTS

| EP | 2508181 A1 | 10/2012 |
| JP | 2016-113441 A | 6/2016 |
| WO | 2008/137692 A1 | 11/2008 |

OTHER PUBLICATIONS

Harvard Medical School. "Medications for Parkinson's disease." Accessed Apr. 10, 2021. Published on Jun. 2006. Available from: <<https://www.health.harvard.edu/newsletter_article/medications_for_parkinson8217s_disease>>. (Year: 2006).*
Endrenyi, L. et al. "Metrics for the Evaluation of Bioequivalence of Modified-Release Formulations." The AAPS Journal. (Dec. 2012), vol. 14, No. 4, pp. 813-819. (Year: 2012).*
Extended European Search Report from the European Patent Office dated Feb. 8, 2021 in Application No. EP 18784304.0.
Kai-Yin Chau et al., "Pramipexole Reduces Phosphorylation of alpha-Synuclein at Serine-129", Journal of Molecular Neuroscience, vol. 51, No. 2, May 18, 2013, pp. 573-580 (8 pages).
Kiren Ubhi et al., "Fluoxetine ameliorates behavioral and neuropathological deficits in a transgenic model mouse of alpha-synucleinopathy", Experimental Neurology, vol. 234, No. 2, Apr. 1, 2012, pp. 405-416 (12 pages).
Laura Marsh, "Depression and Parkinson's Disease: Current Knowledge", Curr Neurol Neurosci Rep., Dec. 2013, pp. 1-17, vol. 13, No. 12.
International Search Report for PCT/US2018/027155 dated, Jun. 20, 2018 (PCT/ISA/210).
Written Opinion of the international Searching Authority for PCT/US2018/027155 dated, Jun. 20, 2018 (PCT/ISA/237).

* cited by examiner

*Primary Examiner* — John S Kenyon
(74) *Attorney, Agent, or Firm* — Sughrue Mion, PLLC

(57) ABSTRACT

The present invention describes the combination of a 6-propylamino-4,5,6,7-tetrahydro-1,3-benzothiazole-2-amine or of a pharmaceutically acceptable salt or solvate thereof with fluoxetine or a pharmaceutically acceptable salt or solvate thereof, for use for treating a synucleinopathy such as Parkinson's disease, Lewy body disease, mutations in the glucocerebrosidase gene, or multiple system atrophy.

7 Claims, No Drawings

PHARMACEUTICAL COMBINATION AND ITS USE FOR TREATING SYNUCLEINOPATHTIES

RELATED APPLICATIONS

This application is a National Stage of International Application No. PCT/US2018/027155 filed Apr. 11, 2018, claims the benefit of U.S. Provisional Patent Application Ser. No. 62/485,082, filed Apr. 13, 2017, the disclosures of which are incorporated herein in their entirety by reference.

FIELD OF THE INVENTION

The present invention pertains to the field of the treatment of synucleinopathies, i.e. of neurodegenerative disorders of the human central nervous system, and in particular of the treatment of neurotoxic processes due to the alpha-synuclein oligomerization and aggregation.

OBJECT OF THE INVENTION

The present invention concerns a pharmaceutical combination comprising 6-propylamino-4,5,6,7-tetrahydro-1,3-benzothiazole-2-amine or a pharmaceutically acceptable salt or solvate thereof and fluoxetine or a pharmaceutically acceptable salt thereof, including fixed-dose combinations, and its use for the treatment of synucleinopathies, in particular the central nervous system neurotoxic effects of alpha-synuclein in a human subject showing an abnormal plasma exosomal/total alpha-synuclein ratio in blood.

DEFINITIONS

"CNS": Central Nervous System.
"IR": Immediate Release of the active ingredient from a composition.
"ER": Extended Release of the active ingredient from a composition.
"GI": Gastro-Intestinal.
"AE(s)": Adverse Effect(s).
"TTS": Transdermal Therapeutic System.
"LBD": Lewy Body Dementia.
"AD": Alzheimer's Disease.
"SNCA gene": Synuclein-alpha or alpha-synuclein gene.
"Synucleinopathy": A disease characterized by the abnormal accumulation, processing and propagation of alpha-synuclein (α-synuclein) in the brain. Namely, α-synuclein deposits in the central, peripheral, and autonomic nervous system. Synucleinopathies (also called α-synucleinopathies) are neurodegenerative diseases which include, but are not limited to Parkinson's disease, Lewy body dementia LBD) or dementia with Lewy bodies (DLB), Alzheimer's disease, the Lewy body variant of AD, multiple system atrophy, neurodegeneration with brain iron accumulation, and parkinsonian disorders associated with glucocerebrosidase (GBA) mutations.
"GBA": Mutations in the glucocerebrosidase gene.
"MSA": Multiple System Atrophy.
"PD": Parkinson's Disease.
"6-Propylamino-4,5,6,7-tetrahydro-1,3-benzothiazole-2-amine": A chiral chemical compound that is available as racemate, chemically (R,S)-6-propylamino-4,5,6,7-tetrahydro-1,3-benzothiazole-2-amine, as (R)-stereoisomer, chemically (R)-6-propylamino-4,5,6,7-tetrahydro-1,3-benzothiazole-2-amine ("dexpramipexole", INN), and as (S)-stereoisomer, chemically (S)-6-propylamino-4,5,6,7-tetrahydro-1,3-benzothiazole-2-amine ("pramipexole", INN). These three chemical entities are basic substances that may be isolated each as an acid addition salt and solvate thereof. Pramipexole dihydrochloride monohydrate is also known with its USAN "pramipexole hydrochloride". As used herein, "6-propylamino-4,5,6,7-tetrahydro-1,3-benzothiazole-2-amine" is a general term that, unless otherwise specified, designates a member selected from the group consisting of pramipexole, the racemate, and a pramipexole/dexpramipexole mixture.
"(R)/(S)-mixture": This term designates a dexpramipexole/pramipexole physical mixture used as an active ingredient according to the present invention.
"(S)-enantiomer": This term, as used herein with reference to 6-propylamino-4,5,6,7-tetrahydro-1,3-benzothiazole-2-amine doses (daily or per unit form) designates the (S)-stereoisomer, included in said doses that, in said 6-propylamino-4,5,6,7-tetrahydro-1,3-benzothiazole-2-amine, is primarily responsible for its dopaminergic action. More specifically, S-enantiomer is herein used to designate the S-stereoisomer that is present in the racemate or pharmaceutically acceptable salt thereof, and similarly, to designate the pramipexole or pharmaceutically acceptable salt thereof that is present, as (S)-constituent, in a (R)/(S)-mixture, in order to distinguish it from pramipexole used alone.
The terms "6-propylamino-4,5,6,7-tetrahydro-1,3-benzothiazole-2-amine", "(R)-6-propylamino-4,5,6,7-tetrahydro-1,3-benzothiazole-2-amine", "dexpramipexole", "pramipexole", "(S)-6-propylamino-4,5,6,7-tetrahydro-1,3-benzothiazole-2-amine", "(S)-enantiomer", "racemate" and "(R)/(S)-mixture" include the free bases and pharmaceutically acceptable salts thereof (unless otherwise specified); and the relative doses (daily or per unit form) are given in equivalents of pramipexole dihydrochloride monohydrate.
"Effective daily dose of pramipexole" or "effective daily dose of (S)-enantiomer": An effective pediatric or adult daily pramipexole or pharmaceutically acceptable salts and solvates thereof dose equivalent to at least the pramipexole dihydrochloride monohydrate approved daily dose for the treatment of PD.
"Effective pramipexole amount (or dose) per unit form" or "effective amount (or dose) per unit form of (S)-enantiomer": An amount per unit form of pramipexole or pharmaceutically acceptable salt or solvate thereof that is equivalent to at least a pramipexole dihydrochloride monohydrate amount per unit form approved for the treatment of PD. More specifically said amount per unit form is equivalent to from 0.125 mg to 20 mg of pramipexole dihydrochloride monohydrate. As noted above and as used herein, "pramipexole" and "(S)-enantiomer" refer to the same chemical entity, but the term "(S)-enantiomer" is generally used when describing the composition of the racemate and of (R)/(S)-mixtures.

BACKGROUND OF THE INVENTION

Alpha-synuclein, a protein composed of 140 amino acids encoded by the SNCA (Synuclein-Alpha) gene, is abundantly expressed in the human brain and to a lesser extent in various other organs. In brain, alpha-synuclein(hereafter also referred to as simply "synuclein") is mainly found in neuronal terminals, especially in the cortex, hippocampus, substantia nigra and cerebellum, where it contributes to the regulation of neurotransmitter release, and passes into the peripheral blood stream (Marques and Outeiro, 2012), in part packaged within exosomal vesicles originating from the CNS (Shi et al, 2014).

Under normal circumstances, this soluble protein appears to form a stably folded tetramer that resists aggregation. But, in certain pathological conditions, for unknown reasons, the alpha-synuclein misfolds, oligomerizes and aggregates (with the formation of fibrils). Somewhere along this aberrant pathway, toxic synuclein species are believed to be formed which also pass into the peripheral (systemic) circulation, carried within exosomes.

Aberrant alpha-synuclein oligomerization and aggregation are thought to be the cause of synucleinopathies, notably PD, LBD, parkinsonian disorders associated with glucocerebrosidase (GBA) mutations, MSA, multiple system atrophy, some forms of Alzheimer's disease, and several other disorders, which are collectively referred to as "synucleinopathies". Alpha-synuclein is a ubiquitous protein that is especially abundant in the brain and has been postulated to play a central role in the pathogenesis of Parkinson's disease (PD), Alzheimer's disease, and other neurodegenerative disorders (Kim et al. 2004).

Synucleinopathies are generally defined as a group of neurodegenerative disorders characterized in part by the intracellular accumulation of abnormal synuclein aggregates, some of which are toxic and contribute to the pathogenesis of the aforementioned disorders.

An abnormal ratio of monomeric to oligomeric synuclein species in plasma exosomes of a patient is proposed to be a diagnostic hallmark of a synucleinopathy and thus, for example, of one of the aforementioned neurodegenerative disorders of the human CNS.

PD is a common neurodegenerative disorder of the human CNS, first described by James Parkinson in 1817. It has three major clinical signs: resting tremor, bradykinesia, and muscular rigidity. In addition, postural instability and various neurobehavioral disabilities may occur. In the U.S. alone it is estimated that over 1 million individuals are afflicted by this inexorably progressive disorder. Moreover, PD prevalence continues to rise along with the general aging of the American population. Parkinsonian signs are now believed to largely reflect a progressive loss of dopaminergic neurons within the nigrostriatal system. The cause of this degenerative process remains incompletely understood, but now appears to involve the misprocessing of alpha-synuclein into abnormal neurotoxic species.

LBD is one of the most common types of progressive dementia. The central features of LBD include progressive cognitive decline, visual hallucinations, and parkinsonian motor symptoms, such as slowness of movement, difficulty walking, and muscular rigidity. Some may also suffer from depression. The symptoms of LBD are caused by the selective loss of nerve cells, presumably a result of synuclein misprocessing and associated with the build-up of Lewy bodies, spherical synuclein accumulations inside many of the degenerating neurons. Researchers do not know why alpha-synuclein accumulates into Lewy bodies or how synuclein species can cause the symptoms of LBD. The formation of LBDs have been considered to be a marker for PD; however, LBDs have also been observed in approximately 60% of both sporadic and familial cases of Alzheimer's disease (AD) (Al-Mansoor et al. 2013). Accordingly, the aggregation of α-synuclein has been strongly implicated as a critical step in the development of neurodegenerative diseases (Al-Mansoor et al. 2013).

Sporadic PD or brainstem-predominant type LBD, and dementia with Lewy bodies (DLB) are the two most frequent α-synucleinopathies, and are progressive multisystem neurodegenerative disorders with widespread occurrence of α-synuclein deposits in the central, peripheral, and autonomic nervous system (Jellinger KA 2008a). Reportedly, there is considerable clinical and pathologic overlap between PD (with or without dementia) and DLB (or LBD), corresponding to Braak LB stages 5 and 6, both frequently associated with variable Alzheimer-type pathology (Jellinger KA 2008a). Dementia often does not correlate with progressed stages of LB pathology, but may also be related to concomitant Alzheimer lesions or mixed pathologies (Jellinger KA, 2008a).

Alzheimer disease (AD) has been reported to be featured by deposition of β-amyloid peptides, phosphorylated tau protein (3- and 4-repeat tau) and frequent α-synuclein (aSyn) deposits (Jellinger KA, 2008b). Lewy body diseases (LBD), such as sporadic Parkinson disease (PD) and dementia with Lewy bodies (DLB), show aSyn-positive deposits in neurons, neurites, glia, and presynaptic terminals, while frontotemporal dementias present tau-positive and tau-negative, ubiquitin- and TDP-43-positive neuronal and glial inclusions (Jellinger KA, 2008b). Molecular interactions between major proteins, which may occur within the same brain in various distribution patterns, cause variable phenotypes and mixed pathologies, e.g. AD with aSyn pathology in the brainstem and amygdala, PD and DLB with AD lesions, and frontotemporal dementia with a mixture of various deposits, while others are featured by one principal pathology without other lesions (e.g. tangle-predominant type of dementia, pure PD, brainstem-predominant LBD) (Jellinger KA, 2008b).

MSA with orthostatic hypotension is the current term for a neurological disorder that was once called Shy-Drager syndrome. A progressive disorder of the central and autonomic nervous systems, it is characterized by orthostatic hypotension (an excessive drop in blood pressure when standing up), which causes dizziness and fainting. Multiple system atrophy can occur without orthostatic hypotension, but instead have urinary tract involvement (urgency/incontinence). Neurologists classify the disorder into 3 types: the parkinsonian-type includes symptoms of Parkinson's disease such as slow movement, stiff muscles, and tremor; the cerebellar-type, which causes problems with coordination and speech; and the combined-type, which includes symptoms of both parkinsonism and cerebellar dysfunction. Problems with urinary incontinence, constipation, and sexual impotence may happen early in the course of the disease. Other symptoms include generalized weakness, double vision or other vision disturbances, difficulty breathing and swallowing, sleep disturbances, and decreased sweating. Because the disease resembles others, a correct diagnosis may take years.

Mutations in the glucocerebrosidase gene (GBA) can result in the autosomal recessive disorder Gaucher disease, Different lines of evidence suggest that mutant GBA may be a risk factor for Parkinson's disease. GBA mutations are now thought to be the single largest risk factor for development of idiopathic PD. Clinically, on imaging and pharmacologically, GBA PD is almost identical to idiopathic PD (O'Regan et al, 2017). The molecular mechanisms which lead to this increased PD risk in GBA mutation carriers are not fully elucidated, but have been shown to be associated with accumulation of synuclein (Soria et al, 2017).

Several other disorders have also, albeit less frequently, been considered synucleinopathies. These include Hallevorden-Spatz syndrome, neuronal axonal dystrophy, and some cases of traumatic brain injury. In the case of Hallevorden-Spatz, symptoms include parkinsonism, dystonia, dysphagia/dysarthria, rigidity or stiffness of the limbs, dementia and spasticity.

Many now believe that processes leading to synuclein oligomerization and aggregation may be central to the cellular injury and destruction occurring in these disorders.

The mechanism of alpha-synuclein aggregation in these synucleinopathies remains poorly understood. Current evidence suggests the conversion of an alpha helical structure into a beta pleated conformation and subsequent oligomerization might be the pathogenic antecedents to the aggregation and fibrillization of synuclein. These characteristics are similar to the aberrant processing of prion proteins that also can become highly neurotoxic. Phosphorylation of alpha-synuclein at the serine-129 residue has been implicated as a contributory factor (Chen et al 2016). According to this author, a prion form of alpha-synuclein could be a causal agent, especially for multiple system atrophy (Prusiner SB et al. 2015). Prions are small proteins that also can misfold, oligomerize, aggregate and propagate to other cells. The result in brain is a profound and spreading neurotoxic process.

Accordingly, inhibiting the initial misfolding, oligomerization and aggregation of synuclein may be beneficial in slowing or even arresting the progression of synucleinopathic disorders.

As mentioned above, alpha-synuclein readily passes into extracellular spaces and has been identified in cerebrospinal fluid, blood, urine, and saliva (Marques and Outeiro, 2012). The mechanisms of alpha-synuclein excretion are not fully understood, but studies have demonstrated that at least a fraction of alpha-synuclein is excreted within exosomes, the 40 nm to 100 nm vesicles of endocytic origin (reviewed in Shi et al. 2014). The ratio of monomeric to oligomeric species in plasma exosomes originating from the CNS may correlate with disease severity (Shi et al. 2014), thus suggesting that plasma exosomal alpha-synuclein and related species can help monitor disease. Similarly, exosomal alpha-synuclein levels correlated with severity of impairment in cross-sectional samples from patients with LBD (Stuendl et al. 2016).

Based on the above, drugs that normalize the ratio of monomeric to oligomeric alpha-synuclein species in plasma exosomes deriving from brain should slow or even arrest the neurodegenerative process associated with the synucleinopathies.

Various compositions for the treatment of PD and related disorders that target the synuclein aggregation pathway have been proposed. The discovery process primarily involves cellular and animal models of prion- and synuclein-induced neurodegeneration (Prusiner SB 2015; Visanji NP et al. 2016). Unfortunately, none of these models has been validated and all are currently regarded uncertain predictors of effects in humans. Nevertheless, these models continue to be widely used in the absence of better discovery techniques.

Pharmaceutical agents currently proposed for consideration include, for instance, such small molecules as (S)-6-propylamino-4,5,6,7-tetrahydro-1,3-benzothiazole-2-amine (pramipexole) and its analogues, alone or in combination with various drugs such as fluoxetine.

Fluoxetine, 1-methylamino-3-phenyl-3-[4-(trifluoromethyl)phenoxy]propane, is a selective serotonin reuptake inhibitor (SSRI) antidepressant. It is currently used in the treatment of major depressive disorder, obsessive-compulsive disorder (OCD), bulimia nervosa, panic disorder, and premenstrual dysphoric disorder. When taken by mouth at recommended maintenance IR-doses (20 mg to 80 mg daily in 1 to 2 divided doses), or ER-dose (90 mg once weekly) by patients with these disorders, fluoxetine typically evinces a high degree of efficacy.

The mechanism by which fluoxetine benefits patients with psycho-affective disorders is generally considered to be linked to the drug's ability to augment CNS serotonin—mediated transmission. In addition, however, large fluoxetine doses in rodents have been shown to induce a significant increase in extracellular concentrations of nor-epinephrine and dopamine after acute systemic administration (Bymaster et al. 2002).

Fluoxetine augments levels of neurotrophic factors such as glial-derived neurotrophic factor (GDNF) and brain-derived neurotrophic factor (BDNF) and, in addition, the effects of fluoxetine in in vivo transgenic models of alpha-synucleinopathy have received careful investigative attention.

It has also been extensively reported to exhibit neuroprotective activity in various cellular and animal models of neurodegenerative disease (Ubhi K et al. 2012).

For example, a laboratory study examined the effect of fluoxetine in the MBP1-hα-syntg mice, a model of MSA (Shults, et al. 2005).

Fluoxetine can protect against 6-OHDA (6-hydroxydopamine) (Suzuki, et al. 2010) and MPTP (1-methyl-4-phenyl-1,2,3,6-tetrahydropyridine) (Chung, et al. 2011)-induced damage in toxin-induced models of PD.

Nevertheless, no evidence has been reported showing that fluoxetine exerts disease modifying effects in humans with a neurodegenerative disease such as PD, or even modifies synuclein species in blood exosomal biomarkers of synucleinopathies of this type.

As mentioned above, (S)-6-propylamino-4,5,6,7-tetrahydro-1,3-benzothiazole-2-amine (pramipexole) and its analogues, alone or in combination with various drugs have also been considered for the treatment of PD and related disorders.

Pramipexole is a synthetic aminothiazole derivative described in U.S. Pat. No. 4,886,812, the content of which is incorporated herein by reference. It is a dopamine agonist of the non-ergoline class (Schneider CS and Mierau J, 1987) that is approved since the late 1990s for the treatment of the symptomatic treatment of Parkinson's disease (PD), in doses ranging from 0.375 mg/day to 4.5 mg/day, given in 3 equally divided doses (Mirapex® Prescribing Information, July 2016). Pramipexole is supplied in tablets for immediate release containing 0.125 mg, 0.25 mg, 0.5 mg, 1 mg and 1.5 mg of pramipexole dihydrochloride monohydrate; and in tablets for extended release containing 4.5 mg of pramipexole dihydrochloride monohydrate.

Although pramipexole is widely used for the relief of parkinsonian symptoms, its potential as a disease modifying agent has made it the object of considerable investigative attention.

Pramipexole reportedly diminishes synuclein oligomer formation in vitro (Ono et al. 2013). Related studies suggest that pramipexole inhibits the toxic effects of rotenone on dopaminergic neurons in a mouse PD model while reducing immunoreactivity for alpha-synuclein; additionally, pramipexole decreases the in vitro oligomerization of human wild-type alpha-synuclein by $H_2O_2$ plus cytochrome c (Inden et al. 2009). Pramipexole has also been observed to inhibit the aggregation of alpha-synuclein in human neuro-blastoma SH5Y cells (Kakimura et al. 2001). Importantly, the relative expression of α-synuclein in serum exosomes has been found to decline during pramipexole treatment of PD-type patients, especially those manifesting acute symptomatic benefit (Luo et al. 2016); an observation of considerable interest since animal model studies have indicated that changes in plasma exosomal synuclein species correlate with changes in the CNS (Shi et al. 2014).

In addition, it began to be reported that pramipexole can exert neuroprotective effects in various in vitro cellular and in vivo animal models of PD. Mechanisms by which these protective effects may occur remain uncertain. Unfortunately, the protective effects of pramipexole in animal models are generally small and require higher doses than considered safe and tolerable for human administration. It is thus hardly surprising that pramipexole, in doses approved for the treatment of motor symptoms of PD failed to evidence neuroprotective (i.e., disease modifying) activity in a randomized, controlled, clinical trial involving 535 PD patients (Schapira et al. 2013).

(R)/(S)-mixtures, consisting of pharmaceutical compositions comprising a therapeutically effective amount of dexpramipexole or pharmaceutically acceptable salts and solvates thereof and a therapeutically effective amount of pramipexole or pharmaceutically acceptable salts and solvates thereof, useful for the treatment of PD, are disclosed in US 2008/0014259, the contents of which are incorporated herein in their entirety by reference.

According to US 2008/0014259, both enantiomers are able to confer neuroprotective effects by their ability to accumulate in brain cells, the spinal cord and mitochondria where they exert a positive effect on neurological function that is independent of the dopamine agonist activity of pramipexole. In particular, said document proposes said composition as a neuroprotective agent and a therapeutically effective amount of from about 0.0625 mg to about 6 mg of pramipexole in combination with up to 5000 mg of dexpramipexole. However, this document emphasizes the pramipexole adverse effects due to its dopaminergic action and tends to privilege pramipexole low doses, as also confirmed by the same applicant in the almost concurrent WO 2008/113003, the contents of which are incorporated herein in their entirety by reference.

According to US 2013/0116292, the contents of which are incorporated herein in their entirety by reference, dexpramipexole, or pharmaceutically acceptable salts and solvates thereof, acts by slowing the progression of neuronal degeneration and/or by preventing neuronal cell death. However, no further mention of this possible noteworthy action of dexpramipexole appeared in the literature.

A synthesis of dexpramipexole and of pharmaceutically acceptable salts thereof, in particular dexpramipexole dihydrochloride monohydrate, is described in US 2012/0253047, the contents of which are incorporated herein in their entirety by reference.

Unfortunately, limitations associated with the administration of pramipexole to synucleinopathic patients limit its use at the potentially higher neuroprotective doses predicted by many animal models. First, mechanisms to explain its putatively beneficial effects on synuclein-related neurotoxicity continue to elude full understanding. Second, effect sizes in animal model studies tend to be small and occur only at relatively high drug doses. Both situations were also observed in the above mentioned report of pramipexole-induced changes in exosomal synuclein in PD patients, which were associated with the administration of the highest—4.5 mg/day—approved dose of pramipexole (Mirapex Package Insert; Revised July 2016).

In the report by Luo et al. (2016), although treatment of Parkinson patients with pramipexole at approved therapeutic doses significantly lowered the relative expression of alpha-synuclein (compared with pre-treatment values), the magnitude of the effect was small. Higher doses of pramipexole could have been more efficacious, but side effects such as vomiting and severe nausea preclude the use of higher doses. For example, Corrigan et al (2000) report that doses of 5 mg/day of pramipexole, hardly higher than the maximum recommended dose of 4.5 mg/day (Pramipexole FDA-approved package Insert) caused nausea in 76% of patients and vomiting in 39% of patients. Furthermore, 36% of patients were not able to complete the study, presumably because of intolerable GI adverse events.

In conclusion, notwithstanding the massive existing literature, in particular Willner et al. 1994, Corrigan et al 2000, and the disclosures of US 2008/0014259, US 2011/0071135 and US 2014/0024644, nobody succeeded in safely increasing pramipexole efficacy, and pramipexole currently provides only marginal activity in the treatment of Parkinson's disease.

There is no clinical demonstration of a neuroprotective effect of pramipexole, or of any disease modifying action by pramipexole, in patients suffering from a synucleinopathic disease such as PD.

Practical limitations associated with the safety and tolerability of administering pramipexole to synucleinopathic patients at the high, neuroprotective doses generally predicted by animal models pose a significant challenge. The effects of pramipexole in animal model studies tend to be small and occur only at relatively high doses. As with most pharmaceuticals, higher doses of pramipexole generally produce more frequent and severe adverse effects along with improved therapeutic efficacy. Side effects of the approved doses, often dose-limiting, include somnolence, confusion, postural hypotension, and hallucinations (Mirapex Package Insert, Revised July 2016).

The document U.S. Pat. No. 6,667,329 (see also WO00/06162), the contents of which are incorporated herewith in their entirety by reference, discloses a combination of pramipexole with another antidepressant for the treatment of depression. Said other antidepressant may be alprazolam, fluoxetine, opipramol, amitriptyline, fluvoxamine, paroxetine, amitriptyline oxide, imipramine, sertraline, chlordiazepoxide, lofepramine, sulpiride, citalopram, maprotiline, tranylcypromine, clomipramine, mianserin, trazodone, quinpirole, mirtazapine, trimipramine, dibenzepin, moclobemide, tryptophan, doxepin, nefazodone, venlafaxine, nortriptyline or viloxazine. According to U.S. Pat. No. 6,667,329, pramipexole combined with another antidepressant has a significantly greater antidepressant activity than either of the two individual components taken alone, the improvement in the effect of pramipexole by the simultaneous administration of another antidepressant having been discovered in tests on rats using the forced swimming test. Said combination may be a fixed-dose combination.

Notwithstanding the knowledge of extensive studies of the effects of fluoxetine and pramipexole, separately, on alpha-synuclein processing over the past ten years, and notwithstanding that the disclosure of the fluoxetine-pramipexole combination in the treatment of the depression was known for about seventeen years, no one has disclosed or suggested a combination of fluoxetine-pramipexole which could be used for treating synucleinopathies, for example PD, or that, at safe and tolerable doses, fluoxetine and pramipexole combined would be found to modify synuclein species in blood exosomes in ways and to degrees indicative of significant disease modifying efficacy.

SUMMARY OF THE INVENTION

The present invention increases the therapeutic window for pramipexole, to safely enable its full neuroprotective efficacy to a degree that delays onset and/or slows symptom progression to a clinically significant extent in those suffering from a synucleinopathy, such as those with PD-like disorders.

One approach to this end is to administer a drug that acts synergistically with pramipexole, to for instance, reduce the minimum effective dose for pramipexole and/or increases pramipexole's efficacy without diminishing its minimum toxic dose. The antidepressant fluoxetine exhibits these properties when combined with pramipexole.

It has now been found that an antidepressant such as fluoxetine acts by augmenting the synucleinopathy-modifying potential of pramipexole in humans, thus allowing at least a slowing of the disease progression at doses that are both safe and tolerable.

In addition, it has been found that an antidepressant such as fluxetine allows for the safe administration of 6-propylamino-4,5,6,7-tetrahydro-1,3-benzothiazole-2-amine at a daily dose comprising a (S)-enantiomer dose that may be higher, and even much higher, than the pramipexole maximum daily dose recommended for the relief of the symptomatic treatment of Parkinson's disease. Consequently, an improvement of the conditions of a patient suffering from a synucleinopathy, in particular PD, Lewy body disease, parkinsonian disorders associated with glucocerebrosidase (GBA) mutations, and MSA is attained.

The combination of an antidepressant such as fluoxetine or of a pharmaceutically acceptable salt or solvate thereof with a 6-propylamino-4,5,6,7-tetrahydro-1,3-benzothiazole-2-amine or a pharmaceutically acceptable salt or solvate thereof, acts to normalize levels of synuclein species in the plasma of patients suffering from a synucleinopathy, in particular by diminishing the concentration of abnormal synuclein species (congeners) in the patient's plasma and in the exosomal vesicles found therein, to a significant degree at doses that are safe and tolerable thus evidencing that said patients will enjoy neuroprotective benefit.

This observation is unexpected since neither drug has been found clinically to possess any disease modifying ability in patients with a synuclein related disorder. Moreover, nowhere has it even been suggested that the combination of these drugs might confer such significant benefit to such individuals since the antiparkinson drug and the antidepressant drug primarily act by very different mechanisms.

The present invention is based on the discovery that an antidepressant such as fluoxetine potentiates (augments) the ability of pramipexole to alter blood exosomal synuclein species in ways indicating the activation of a central neuroprotective mechanism, i.e. reducing oligomerization of synuclein:

these changes occur at safe and tolerable doses of both drugs; and these changes are indicative of CNS changes that will confer disease clinical improvement in a way and to a degree that will provide practical and significant disease modifying benefit to sufferers.

The findings are unexpected since, in spite of numerous publications on pramipexole and on fluoxetine and their combination, no observations on this possibility were reported, mentioned or suggested, and no speculation on its consequences were found. Moreover, it is unexpected since the two drugs act on different targets, by different mechanisms, to produce different clinical effects, and thus would hardly be expected to have synergistic effects in the manner disclosed herein.

In addition, it has also surprisingly been found that an antidepressant such as fluoxetine attenuates the GI adverse effects of pramipexole, thus allowing the safe administration of pramipexole within the whole pramipexole recommended daily dose range (0.375 mg-4.5 mg) and also at doses higher than the maximum recommended daily dose, for example from 4.5 mg to 6 mg, from more than 6 mg to 10 mg, from 6.5 mg to 10 mg and even from 6.5 mg to 15 mg or from 6.5 mg to 20 mg.

These findings thus allow the treatment of disabling synucleinopathies such as PD, LBD, mutations in the glucocerebrosidase (GBA) gene, Alzheimer's disease, the Lewy body variant of AD, neurodegeneration with brain iron accumulation, and MSA.

Thus, the present invention provides a method for treating a patient suffering from a synucleinopathy, which comprises administering to said patient in need of said treatment an antidepressant such as fluoxetine or a pharmaceutically acceptable salt or solvate thereof in combination with a 6-propylamino-4,5,6,7-tetrahydro-1,3-benzothiazole-2-amine or of a pharmaceutically acceptable salt or solvate thereof.

Pharmaceutically acceptable salts of 6-propylamino-4,5,6,7-tetrahydro-1,3-benzothiazole-2-amine are also included in the present invention.

The invention also provides a combination of an antidepressant such as fluoxetine or of a pharmaceutically acceptable salt or solvate thereof, normally at a daily dose that is at least as high as the dose approved for the prevention or treatment of depression, and an effective daily dose of a 6-propylamino-4,5,6,7-tetrahydro-1,3-benzothiazole-2-amine or a pharmaceutically acceptable salt or solvate thereof, for use for the treatment of synucleinopathies.

Preferably, the method for treating a patient suffering from a synucleinopathy according to the present invention comprises administering to said patient in need of said treatment, an effective daily dose of fluoxetine hydrochloride that is at least as high as the dose approved for the treatment of depression, and an effective daily dose of pramipexole dihydrochloride monohydrate.

According to an embodiment, fluoxetine or a pharmaceutically acceptable salt or solvate thereof and the 6-propylamino-4,5,6,7-tetrahydro-1,3-benzothiazole-2-amine or a pharmaceutically acceptable salt or solvate thereof are each formulated in a pharmaceutical composition in admixture with a pharmaceutical carrier and concurrently or sequentially administered to a patient in need of said treatment.

According to another embodiment, fluoxetine or a pharmaceutically acceptable salt or solvate thereof and the 6-propylamino-4,5,6,7-tetrahydro-1,3-benzothiazole-2-amine or a pharmaceutically acceptable salt or solvate thereof are mixed together and formulated in a pharmaceutical composition (fixed-dose combination) in admixture with a pharmaceutical carrier, to be administered to the patient in need of said treatment.

According to an advantageous embodiment, in the method (or use) for the treatment of a synucleinopathy, fluoxetine or a pharmaceutically acceptable salt or solvate thereof is formulated in a pharmaceutical composition in admixture with a pharmaceutical carrier or vehicle. This composition is administered to a patient in need of said treatment at a daily dose that is equivalent to from 5 mg to 90 mg of fluoxetine base, in combination with a 6-propylamino-4,5,6,7-tetrahydro-1,3-benzothiazole-2-amine or pharmaceutically acceptable salt or solvate thereof. Said 6-propylamino-4,5,6,7-tetrahydro-1,3-benzothiazole-2-amine is also formulated in a pharmaceutical composition in admixture with a pharmaceutical carrier or vehicle and is administered to said patient in need of said treatment at a daily dose that is equivalent to from 1.5 mg to 3000 mg of pramipexole dihydrochloride monohydrate, said daily dose including an (S)-enantiomer daily dose equivalent to from 1.5 to 20 mg, from 1.5 mg to 15 mg, from 1.5 mg to 10 mg, from 1.5 mg to 7.5 mg, or from 1.5 mg to 6 mg of pramipexole dihydrochloride monohydrate.

In said method (or use), said fluoxetine and said 6-propylamino-4,5,6,7-tetrahydro-1,3-benzothiazole-2-amine combination is administered to said patient in a fixed-dose combination wherein said fluoxetine and said 6-propylamino-4,5,6,7-tetrahydro-1,3-benzothiazole-2-amine are mixed together, and with a pharmaceutical carrier or vehicle.

Preferably, fluoxetine is used as fluoxetine hydrochloride and the 6-propylamino-4,5,6,7-tetrahydro-1,3-benzothiazole-2-amine is used as pramipexole dihydrochloride monohydrate.

DETAILED DESCRIPTION

The present invention is based on the discovery that the an antidepressant agent such as fluoxetine will synergistically and substantially improve the ability of safe and tolerable doses of 6-propylamino-4,5,6,7-tetrahydro-1,3-benzothiazole-2-amine to reduce toxic synuclein oligomers in plasma exosomes of patients with PD and related synucleinopathic disorders, and thus benefit patients with such fatal disorders to a previously unrealized degree.

As set forth above, these results are totally unexpected since the ability of fluoxetine to augment the biomarker response to pramipexole to a degree that confers clinical patient benefit has never before been described, suggested or even anticipated in view of the lack of a rational basis and differences in the drugs' pharmacologic properties including their mechanisms of action; and no drug or drug combination, let alone this particular combination, has ever been found to have convincing neuroprotective efficacy potential in humans with synucleinopathies.

Specific Aspects of the Invention

Thus, according to a first aspect, the present invention provides a method for treating a patient suffering from a synucleinopathy, which comprises administering to a patient in need of said treatment an effective yet tolerable daily dose of fluoxetine or a pharmaceutically acceptable salt or solvate thereof in combination with an effective daily dose of a 6-propylamino-4,5,6,7-tetrahydro-1,3-benzothiazole-2-amine or a pharmaceutically acceptable salt thereof.

Herein below, the expressions "salts or solvates thereof" and "salts and solvates thereof", in reference to fluoxetine or a 6-propylamino-4,5,6,7-tetrahydro-1,3-benzothiazole-2-amine, indicate that the salt of said fluoxetine or said 6-propylamino-4,5,6,7-tetrahydro-1,3-benzothiazole-2-amine may be solvated with a solvent, normally water.

Herein, "fluoxetine" stands for 1-methylamino-3-phenyl-3-[4-(trifluoromethyl)phenoxy]propane as the free base or a salt or solvate thereof. Fluoxetine may be used as free base or as its hydrochloride salt.

The 6-propylamino-4,5,6,7-tetrahydro-1,3-benzothiazole-2-amine is selected from the group consisting of (R,S)-6-propylamino-4,5,6,7-tetrahydro-1,3-benzothiazole-2-amine (as the racemate) and pharmaceutically acceptable salts and solvates thereof;

(S)-propylamino-4,5,6,7-tetrahydro-1,3-benzothiazole-2-amine (INN: pramipexole) and pharmaceutically acceptable salts thereof, in particular its dihydrochloride monohydrate (USAN: pramipexole hydrochloride); and a (R)/(S)-mixture consisting of a pharmaceutical composition comprising an effective amount of dexpramipexole and an effective amount of pramipexole, said pramipexole being referred to as "(S)-enantiomer" in said (R)/(S)-mixtures.

The neuroprotective activity of (R)-propylamino-4,5,6,7-tetrahydro-1,3-benzothiazole-2-amine or pharmaceutically acceptable salts and solvates thereof, that is not dopaminergic, is disclosed in US 2013/0116292, the contents of which are incorporated herein in their entirety by reference. According to this document, said (R)-propylamino-4,5,6,7-tetrahydro-1,3-benzothiazole-2-amine or pharmaceutically acceptable salts and solvates thereof acts by slowing the progression of neuronal degeneration and/or by preventing neuronal cell death.

(R)/(S)-mixtures, consisting of pharmaceutical compositions comprising a therapeutically effective amount of (R)-propylamino-4,5,6,7-tetrahydro-1,3-benzothiazole-2-amine or pharmaceutically acceptable salts and solvates thereof and a therapeutically effective amount of (S)-propylamino-4,5,6,7-tetrahydro-1,3-benzothiazole-2-amine are disclosed in the aforementioned US 2008/0014259, the contents of which are incorporated herein in their entirety by reference.

The term "effective daily dose of fluoxetine", as used herein, refers to a daily dose of fluoxetine hydrochloride equivalent to a fluoxetine base dose that is at least as high as an approved daily dose for the treatment of depression.

As set forth in the definitions, "fluoxetine" generally stands for the active principle per se, independently of the salt or solvate of said active principle, and "6-propylamino-4,5,6,7-tetrahydro-1,3-benzothiazole-2-amine" generally stands for the active principle per se, independently of the steric configuration and of the salt or solvate of said active principle.

In particular, the term "fluoxetine" includes the free base and pharmaceutically acceptable salts and solvates thereof, their doses per unit form or their daily doses being expressed as equivalents of fluoxetine base; and the term "6-propylamino-4,5,6,7-tetrahydro-1,3-benzothiazole-2-amine" refers to 6-propylamino-4,5,6,7-tetrahydro-1,3-benzothiazole-2-amine and pharmaceutically acceptable salts and solvates thereof, their doses per unit form or their daily doses being expressed as equivalents of pramipexole dihydrochloride monohydrate.

Pharmaceutically acceptable salts or solvates of fluoxetine and of 6-propylamino-4,5,6,7-tetrahydro-1,3-benzothiazole-2-amine are also included in the present invention. Illustrative examples of these salts include acid addition salts with mineral acids such as hydrochloric acid, hydrobromic acid, hydriodic acid, sulfuric acid, nitric acid, phosphoric acid and the like or with organic acids such as formic acid, acetic acid, propionic acid, oxalic acid, malonic acid, succinic acid, fumaric acid, maleic acid, lactic acid, malic acid, tartaric acid, citric acid, carbonic acid, methanesulfonic acid, ethanesulfonic acid, aspartic acid, glutamic acid and the like. The solvation agent is generally water.

In the method (or use) for the treatment of a synucleinopathy such as PD, LBD, AD, mutations in the glucocerebrosidase gene, and MSA, fluoxetine or a pharmaceutically acceptable salt or solvate thereof is formulated in a pharmaceutical composition in admixture with a pharmaceutical carrier or vehicle. This composition is administered to a patient in need of said treatment at a daily dose that is equivalent to from 5 mg to 90 mg of fluoxetine base, in combination with a 6-propylamino-4,5,6,7-tetrahydro-1,3-benzothiazole-2-amine or pharmaceutically acceptable salt or solvate thereof. Said 6-propylamino-4,5,6,7-tetrahydro-1,3-benzothiazole-2-amine is also formulated in a pharmaceutical composition in admixture with a pharmaceutical carrier or vehicle and is administered to said patient in need of said treatment at a daily dose that is equivalent to from 1.5 mg to 3000 mg of pramipexole dihydrochloride monohydrate, said daily dose including an (S)-enantiomer daily dose equivalent to from 1.5 to 20 mg, from 1.5 mg to 15 mg, from 1.5 mg to 10 mg, from 1.5 mg to 7.5 mg, or from 1.5 mg to 6 mg of pramipexole dihydrochloride monohydrate.

In said pharmaceutical composition, the 6-propylamino-4,5,6,7-tetrahydro-1,3-benzothiazole-2-amine or pharmaceutically acceptable salt or solvate thereof is selected from the group consisting of (S)-6-propylamino-4,5,6,7-tetrahydro-1,3-benzothiazole-2-amine or a pharmaceutically acceptable salts and solvates thereof, in an amount per unit form equivalent to from 0.125 mg to 20 mg of pramipexole dihydrochloride monohydrate;

(R,S)-6-propylamino-4,5,6,7-tetrahydro-1,3-benzothiazole-2-amine (the racemate) and pharmaceutically acceptable salts and solvates thereof, in an amount per unit form equivalent to from 0.25 mg to 40 mg of pramipexole dihydrochloride monohydrate; and a (R)/(S)-mixture. comprising 6-propylamino-4,5,6,7-tetrahydro-1,3-benzothiazole-2-amine, in an amount per unit form equivalent to from 50 mg to 3000 mg of pramipexole dihydrochloride monohydrate, said amount per unit form including a (S)-enantiomer amount equivalent to from 0.125 mg to 20 mg of pramipexole dihydrochloride monohydrate and (R)-6-propylamino-4,5,6,7-tetrahydro-1,3-benzothiazole-2-amine, in an amount equivalent to from 50 mg to 3000 mg (minus from 0.125 mg to 20 mg) of pramipexole dihydrochloride monohydrate.

Normally, in the pharmaceutical composition to be administered in combination with the above illustrated fluoxetine pharmaceutical composition, the 6-propylamino-4,5,6,7-tetrahydro-1,3-benzothiazole-2-amine is preferably selected from the group consisting of (S)-6-propylamino-4,5,6,7-tetrahydro-1,3-benzothiazole-2-amine (INN: pramipexole) and pharmaceutically acceptable salts and solvates thereof, in particular its dihydrochloride monohydrate (USAN: pramipexole hydrochloride), in a dose per unit form equivalent to from 0.125 mg to 20 mg, from 0.125 mg to 15 mg, from 0.125 mg to 10 mg, from 0.125 mg to 7.5 mg, or from 0.125 mg to 6 mg of pramipexole dihydrochloride monohydrate;

(R,S)-6-propylamino-4,5,6,7-tetrahydro-1,3-benzothiazole-2-amine (the racemate) and pharmaceutically acceptable salts an solvates thereof, in a dose per unit form equivalent to from 0.25 mg to 40 mg, from 0.25 mg to 30 mg, from 0.25 mg to 20 mg, from 0.25 mg to 15 mg, or from 0.25 mg to 12 mg of pramipexole dihydrochloride monohydrate (thus, obviously, including a dose per unit form of (S)-enantiomer equivalent to from 0.125 mg to 20 mg, from 0.125 mg to 15 mg, from 0.125 mg to 10 mg, from 0.125 mg to 7.5 mg, or from 0.125 mg to 6 mg of pramipexole dihydrochloride monohydrate, and a dose per unit form of (R)-6-propylamino-4,5,6,7-tetrahydro-1, 3-benzothiazole-2-amine equivalent to from 0.125 mg to 20 mg, from 0.125 mg to 15 mg, from 0.125 mg to 10 mg, from 0.125 mg to 7.5 mg, or from 0.125 mg to 6 mg of pramipexole dihydrochloride monohydrate); and (R)/(S)-mixture. i.e. a pharmaceutical composition in dosage unit form comprising 6-propylamino-4,5,6,7-tetrahydro-1,3-benzothiazole-2-amine, at a dose per unit form equivalent to from 50 mg to 3000 mg, preferably to from 150 mg to 3000 mg, of pramipexole dihydrochloride monohydrate, said amount per unit form including a (S)-enantiomer amount equivalent to from 0.125 mg to 20 mg, from 0.125 mg to 15 mg, from 0.125 mg to 10 mg, from 0.125 mg to 7.5 mg, or from 0.125 mg to 6 mg of pramipexole dihydrate monohydrate, thus, obviously, said amount per unit form being constituted by an amount of (S)-enantiomer equivalent to from 0.125 mg to 20 mg, from 0.125 mg to 15 mg, from 0.125 mg to 10 mg, from 0.125 mg to 7.5 mg, or from 0.125 mg to 6 mg of pramipexole dihydrochloride monohydrate and by a (R)-6-propylamino-4,5,6,7-tetrahydro-1,3-benzothiazole-2-amine amount per unit form equivalent to from 50 mg (or 150 mg) to 3000 mg (minus from 0.125 mg to 20 mg, from 0.125 mg to 15 mg, from 0.125 mg to 10 mg, from 0.125 mg to 7.5 mg, or from 0.125 to 6 mg) of pramipexole dihydrochloride monohydrate).

The dose of the 6-propylamino-4,5,6,7-tetrahydro-1,3-benzothiazole-2-amine, per IR-unit form, will range from 0.125 mg to 1500 mg, said dose including a (S)-isomer amount per IR-form equivalent to from 0.125 mg to 10 mg, from 0.125 mg to 7.5 mg, from 0.125 mg to 5 mg, from 0.125 mg to 3.75 mg, or from 0.125 to 3 mg of pramipexole dihydrochloride monohydrate, depending on safety and tolerability (in combination with fluoxetine, in the above dose/unit form).

The dose of the 6-propylamino-4,5,6,7-tetrahydro-1,3-benzothiazole-2-amine, per ER-unit form, will range from 0.375 mg to 3000 mg, said dose including a (S)-isomer amount per ER-form equivalent to from 0.375 mg to 20 mg, from 0.375 mg to 15 mg, from 0.375 mg to 10 mg, from 0.375 mg to 7.5 mg, or from 0.375 to 6 mg of pramipexole dihydrochloride monohydrate, depending on safety and tolerability (in combination with fluoxetine, in the above dose/unit form).

The dose of pramipexole or pharmaceutically acceptable salt thereof, per IR-unit form, will be equivalent to from 0.125 mg to 10 mg, from 0.125 mg to 7.5 mg, from 0.125 mg to 5 mg, from 0.125 mg to 3.75 mg, or from 0.125 mg to 3 mg of pramipexole dihydrochloride monohydrate, depending on safety and tolerability (in combination with fluoxetine, in the above dose/unit form).

The dose of pramipexole or pharmaceutically acceptable salt thereof, per ER-unit form, will be equivalent to from 0.375 mg to 20 mg, from 0.375 mg to 15 mg, from 0.375 mg to 10 mg, from 0.375 mg to 7.5 mg, or from 0.375 mg to 6 mg of pramipexole dihydrochloride monohydrate, depending on safety and tolerability (in combination with fluoxetine, in the above dose/unit form).

According to a second aspect, the invention provides a pharmaceutical combination comprising (a) fluoxetine, at a dose that is at least as high as a dose approved for the treatment of depression, and (b) a 6-propylamino-4,5,6,7-tetrahydro-1,3-benzothiazole-2-amine or a pharmaceutically acceptable salt or solvate thereof, for use for the treatment of a synucleinopathy.

According to an embodiment of this second aspect, the invention provides fluoxetine, in a pharmaceutical composition comprising, as an active ingredient, fluoxetine or a pharmaceutically acceptable salt or solvate thereof, in admixture with a pharmaceutical carrier or vehicle, for use for the treatment of a synucleinopathy in combination with 6-propylamino-4,5,6,7-tetrahydro-1,3-benzothiazole-2- amine, also in a pharmaceutical composition in admixture with a pharmaceutical carrier or vehicle.

According to this embodiment, said fluoxetine, or a pharmaceutically acceptable salt or solvate thereof, is present in said composition in an amount/unit form, in fluoxetine, at least as high as a dose/unit form approved for the treatment of depression, in admixture with a pharmaceutical carrier, for use for the treatment of a synucleinopathy, in combination with pramipexole or a pharmaceutically acceptable salt or solvate thereof in doses, in pramipexole dihydrochloride monohydrate, approved for the relief of the symptoms of PD.

According to a third aspect, the invention provides the use of fluoxetine for the preparation of a medicament consisting of a pharmaceutical composition comprising, as an active ingredient, said fluoxetine, or a pharmaceutically acceptable salt or solvate thereof, in admixture with a pharmaceutical carrier or vehicle, for the treatment of a synucleinopathy in combination with a 6-propylamino-4,5,6,7-tetrahydro-1,3-benzothiazole-2-amine or of a pharmaceutically acceptable salt and/or solvate thereof, preferably with pramipexole or a pharmaceutically acceptable salt thereof.

Said use and said treatment of synucleinopathies according to the above second aspect and third aspect of the invention are described in the above disclosure of the first aspect of the invention.

According to a fourth aspect, the invention provides the use of fluoxetine for the preparation of a medicament for the treatment of a synucleinopathy in a patient in need of said treatment, said medicament consisting of a pharmaceutical composition in dosage unit form comprising, as an active ingredient said fluoxetine and, as a second active ingredient, 6-propylamino-4,5,6,7-tetrahydro-1,3-benzothiazole-2-amine, in admixture with a pharmaceutical carrier or vehicle.

In particular, the invention provides a pharmaceutical fixed-dose combination consisting of a pharmaceutical composition in dosage unit form comprising fluoxetine or a pharmaceutically acceptable salt or solvate thereof, as Component (a) and a 6-propylamino-4,5,6,7-tetrahydro-1,3-benzothiazole-2-amine or a pharmaceutically acceptable salt or solvate thereof, preferably with pramipexole or a pharmaceutically acceptable salt thereof, as Component (b), in admixture with a pharmaceutical carrier or vehicle According to an embodiment of this fourth aspect, the invention provides a fixed-dose combination consisting of a pharmaceutical composition comprising
(a) fluoxetine hydrochloride, in an amount/unit form (in fluoxetine base) at least at least as high as the amount/unit form, in fluoxetine base, approved for the treatment of depression; and
(b) pramipexole dihydrochloride monohydrate, in an amount/unit form at least at least as high as an amount/unit form approved for the treatment of Parkinson's disease, in admixture with a pharmaceutical carrier or vehicle,
for use for the treatment of synucleinopathies.

Moreover, according to an embodiment of this fourth aspect, the invention provides the use of
(a) fluoxetine hydrochloride, in an amount/unit form (in fluoxetine base) at least as high as the amount/unit form, in fluoxetine base, approved for the treatment of depression; and
(b) pramipexole dihydrochloride monohydrate, in an amount/unit form at least at least as high as an amount/unit form approved for the treatment of Parkinson's disease, for the preparation of a medicament consisting of a pharmaceutical composition comprising said fluoxetine and said pramipexole dihydrochloride monohydrate, in admixture with a pharmaceutical carrier or vehicle, for the treatment of synucleinopathies.

In the above compositions according to this fourth aspect, fluoxetine or a pharmaceutically acceptable salt thereof Component (a) is present in an amount equivalent to from 2 mg to 90 mg of fluoxetine hydrochloride and said 6-propylamino-4,5,6,7-tetrahydro-1,3-benzothiazole-2-amine or a pharmaceutically acceptable salt and/or solvate thereof is present in an amount equivalent to of from 0.125 mg to 3000 mg of pramipexole dihydrochloride monohydrate, said amount including an S-enantiomer amount equivalent to from 0.125 mg to 20 mg of pramipexole dihydrochloride monohydrate. Preferably, in the above compositions, said 6-propylamino-4,5,6,7-tetrahydro-1,3-benzothiazole-2-amine is pramipexole or a pharmaceutically acceptable salt thereof, in an amount equivalent to from 0.125 mg to 20 mg of pramipexole dihydrochloride monohydrate.

The dose of fluoxetine, or of a pharmaceutically acceptable salt or solvate thereof, per IR-unit form, will be in an amount that is equivalent to from 2 mg to 40 mg or from 5 mg to 40 mg of fluoxetine base, depending on safety and tolerability (in combination with 6-propylamino-4,5,6,7-tetrahydro-1,3-benzothiazole-2-amine). Preferably, said fluoxetine pharmaceutically acceptable salt is fluoxetine hydrochloride in the above IR-dose/unit form.

The dose/unit form of fluoxetine, or of a pharmaceutically acceptable salt or solvate thereof, in an ER-formulation, including slow-release compositions and transdermal therapeutic systems such as transdermal patches, will be in an amount (in fluoxetine) of from 20 mg to 90 mg, depending on safety and tolerability (in combination with a 6-propylamino-4,5,6,7-tetrahydro-1,3-benzothiazole-2-amine).

In particular, according to an embodiment of this fourth aspect, the invention, provides a fixed-dose combination consisting of a pharmaceutical composition which comprises
(a) fluoxetine, in an amount per unit form of from 2 mg to 90 mg; and
(b) a 6-propylamino-4,5,6,7-tetrahydro-1,3-benzothiazole-2-amine selected from the group consisting of
  (S)-6-propylamino-4,5,6,7-tetrahydro-1,3-benzothiazole-2-amine or a pharmaceutically acceptable salts and solvates thereof, in an amount per unit form equivalent to from 0.125 mg to 20 mg of pramipexole dihydrochloride monohydrate;
  (R,S)-6-propylamino-4,5,6,7-tetrahydro-1,3-benzothiazole-2-amine (the racemate) and pharmaceutically acceptable salts an solvates thereof, in an amount per unit form equivalent to from 0.25 mg to 40 mg of pramipexole dihydrochloride monohydrate; and
  a (R)/(S)-mixture comprising 6-propylamino-4,5,6,7-tetrahydro-1,3-benzothiazole-2-amine, in an amount per unit form equivalent to from 50 mg to 3000 mg, said amount per unit form including a (S)-enantiomer amount equivalent to from 0.125 mg to 20 mg of pramipexole dihydrochloride monohydrate and (R)-6-propylamino-4,5,6,7-tetrahydro-1,3-benzothiazole-2-amine, in an amount equivalent to from 50 mg to 3000 mg (minus from 0.125 mg to 20 mg) of pramipexole dihydrochloride monohydrate;
  in admixture with a pharmaceutical carrier or vehicle.

In the pharmaceutical composition to be administered in combination with the above illustrated fluoxetine pharmaceutical composition, for example in the fixed-dose combination according this fourth aspect of the invention, the 6-propylamino-4,5,6,7-tetrahydro-1,3-benzothiazole-2-amine is preferably selected from the group consisting of (S)-6-propylamino-4,5,6,7-tetrahydro-1,3-benzothiazole-2-amine (INN: pramipexole) and pharmaceutically acceptable salts and solvates thereof, in particular its dihydrochloride monohydrate (USAN: pramipexole hydrochloride), in a dose per unit form equivalent to from 0.125 mg to 20 mg, from 0.125 mg to 15 mg, from 0.125 mg to 10 mg, from 0.125 mg to 7.5 mg, or from 0.125 mg to 6 mg of pramipexole dihydrochloride monohydrate;

(R,S)-6-propylamino-4,5,6,7-tetrahydro-1,3-benzothiazole-2-amine (the racemate) and pharmaceutically acceptable salts an solvates thereof, in a dose per unit form equivalent to from 0.25 mg to 40 mg, from 0.25 mg to 30 mg, from 0.25 mg to 20 mg, from 0.25 mg to 15 mg, or from 0.25 mg to 12 mg of pramipexole dihydrochloride monohydrate (thus, obviously, including a dose per unit form of (S)-enantiomer equivalent to from 0.125 mg to 20 mg, from 0.125 mg to 15 mg, from 0.125 mg to 10 mg, from 0.125 mg to 7.5 mg, or from 0.125 mg to 6 mg of pramipexole dihydrochloride monohydrate, and a dose per unit form of (R)-6-propylamino-4,5,6,7-tetrahydro-1,3-benzothiazole-2-amine equivalent to from 0.125 mg to 20 mg, from 0.125 mg to 15 mg, from 0.125 mg to 10 mg, from 0.125 mg to 7.5 mg, or from 0.125 mg to 6 mg of pramipexole dihydrochloride monohydrate); and (R)/(S)-mixture comprising 6-propylamino-4,5,6,7-tetrahydro-1,3-benzothiazole-2-amine, at a dose per unit form equivalent to from 50 mg to 3000 mg, preferably to from 150 mg to 3000 mg, of pramipexole dihydrochloride monohydrate, said amount per unit form including a (S)-enantiomer amount equivalent to from 0.125 mg to 20 mg, from 0.125 mg to 15 mg, from 0.125 mg to 10 mg, from 0.125 mg to 7.5 mg, or from 0.125 mg to 6 mg of pramipexole dihydrochloride monohydrate, thus, obviously, said amount per unit form being constituted by an amount of (S)-enantiomer equivalent to from 0.125 mg to 20 mg of pramipexole dihydrochloride monohydrate and by a (R)-6-propylamino-4,5,6,7-tetrahydro-1,3-benzothiazole-2-amine amount per unit form equivalent to from 50 mg (or 150 mg) to 3000 mg (minus from 0.125 mg to 20 mg, from 0.125 mg to 15 mg, from 0.125 mg to 10 mg, from 0.125 mg to 7.5 mg, or from 0.125 mg to 6 mg) of pramipexole dihydrochloride monohydrate.

The dose of the 6-propylamino-4,5,6,7-tetrahydro-1,3-benzothiazole-2-amine, per IR-unit form, will range from 0.125 mg to 1500 mg, said dose including a (S)-isomer amount per IR-form equivalent to from 0.125 mg to 10 mg, from 0.125 mg to 7.5 mg, from 0.125 mg to 5 mg, from 0.125 mg to 3.75 mg, or from 0.125 to 3 mg of pramipexole dihydrochloride monohydrate, depending on safety and tolerability (in combination with fluoxetine, in the above dose/unit form).

The dose of pramipexole or pharmaceutically acceptable salt thereof, per IR-unit form, will be equivalent to from 0.125 mg to 10 mg, from 0.125 mg to 7.5 mg, from 0.125 mg to 5 mg, from 0.125 mg to 3.75 mg, or from 0.125 mg to 3 mg of pramipexole dihydrochloride monohydrate, depending on safety and tolerability (in combination with fluoxetine, in the above dose/unit form).

If said 6-propylamino-4,5,6,7-tetrahydro-1,3-benzothiazole-2-amine or pharmaceutically acceptable salt of solvate thereof is pramipexole dihydrochloride monohydrate, the dose-range is from 0.125 mg to 10 mg, from 0.125 mg to 7.5 mg, from 0.125 mg to 5 mg, from 0.125 mg to 3.75 mg, or from 0.125 mg to 3 mg per IR-unit form, depending on safety and tolerability (in combination with fluoxetine, at the above dose/unit form).

The dose/unit form of 6-propylamino-4,5,6,7-tetrahydro-1,3-benzothiazole-2-amine in an ER formulation, including slow-release compositions and transdermal therapeutic systems such as transdermal patches, will range from 1.5 mg to 3000 mg, said dose/unit form including a (S)-isomer amount per ER-form equivalent to from 1.5 mg to 20 mg, from 1.5 mg to 15 mg, from 1.5 mg to 10 mg, from 1.5 mg to 7.5 mg, or from 1.5 to 6 mg of pramipexole dihydrochloride monohydrate, depending on the tolerability in combination with fluoxetine, at the above dose/unit form.

The dose of pramipexole or pharmaceutically acceptable salt thereof, per ER-unit form, will be equivalent to from 1.5 mg to 20 mg, from 1.5 mg to 15 mg, from 1.5 mg to 10 mg, from 1.5 mg to 7.5 mg, or from 1.5 mg to 6 mg of pramipexole dihydrochloride monohydrate, depending on safety and tolerability (in combination with fluoxetine, in the above dose/unit form).

Normally, if said 6-propylamino-4,5,6,7-tetrahydro-1,3-benzothiazole-2-amine is pramipexole dihydrochloride monohydrate or pramipexole base, the dose-range/unit form (in pramipexole dihydrochloride monohydrate), will be from 1.5 mg to 20 mg, from 1.5 mg to 15 mg, from 1.5 mg to 10 mg, from 1.5 mg to 7.5 mg or from 1.5 mg to 6 mg per ER-unit form.

For the use of the combination of the present invention in the treatment of synucleinopathies, fluoxetine or a pharmaceutically acceptable salt thereof is administered, preferably as fluoxetine hydrochloride, at a daily dose (in fluoxetine base) of from 4 mg to 40 mg in a IR-or ER-form or at a weekly dose of 90 mg, in an ER-form; and the 6-propylamino-4,5,6,7-tetrahydro-1,3-benzothiazole-2-amine or pharmaceutically acceptable salt thereof is administered at a daily dose equivalent to from 1.5 mg to 3000 mg of pramipexole dihydrochloride monohydrate in IR- or ER-form, said daily dose including a (S)-isomer amount per IR- or ER-form equivalent to from 1.5 mg to 20 mg, from 1.5 mg to 15 mg, from 1.5 mg to 10 mg, from 1.5 mg to 7.5 mg, or from 1.5 to 6 mg of pramipexole dihydrochloride monohydrate.

If, in said combination, said 6-propylamino-4,5,6,7-tetrahydro-1,3-benzothiazole-2-amine is pramipexole or a pharmaceutically acceptable salt thereof, it is administered at a daily dose that is equivalent to from 1.5 mg to 20 mg, from 1.5 mg to 15 mg, from 1.5 mg to 10 mg, from 1.5 mg to 7.5 mg, or from 1.5 mg to 6 mg of pramipexole dihydrochloride monohydrate, preferably as pramipexole dihydrochloride monohydrate at a daily dose of from 1.5 mg to 20 mg, from 1.5 mg to 15 mg, from 1.5 mg to 10 mg, from 1.5 mg to 7.5 mg, or from 1.5 mg to 6 mg.

As described above, for the intended use, the combination of the invention comprises (a) fluoxetine or a pharmaceutically acceptable salt or solvate thereof; and (b) a 6-propylamino-4,5,6,7-tetrahydro-1,3-benzothiazole-2-amine or a pharmaceutically acceptable salt or solvate thereof, each in a pharmaceutical composition in admixture with a pharmaceutical carrier or vehicle; or (a/b) fluoxetine or a pharmaceutically acceptable salt or solvate thereof; and a 6-propylamino-4,5,6,7-tetrahydro-1,3-benzothiazole-2-amine or a pharmaceutically acceptable salt or solvate thereof, mixed together in a pharmaceutical composition in dosage unit form, in admixture with a pharmaceutical carrier or vehicle, as a fixed dose combination.

In the pharmaceutical compositions of the present invention for oral, subcutaneous, intravenous, transdermal or topical administration, the active ingredients are preferably administered in the form of dosage units, in admixture with the classic pharmaceutical carriers or vehicles.

The dosage, i.e. the amount of active ingredient in a single dose to be administered to a patient suffering from a synucleinopathy patient, can vary widely depending on the age, weight, and the health condition of the patient, as also illustrated herein above. This dosage includes the administration of a dose per unit form of from 2 mg to 40 mg of fluoxetine, and from 0.125 mg to 1500 mg of 6-propylamino-4,5,6,7-tetrahydro-1,3-benzothiazole-2-amine, according to the age of the patient, from one to three times a day by intravenous, subcutaneous, oral, or transcutaneous administration, according to the strength of the doses of the each of the active ingredients.

If fluoxetine is as hydrochloride, said dosage is from 2 mg to 90 mg (in fluoxetine base).

If 6-propylamino-4,5,6,7-tetrahydro-1,3-benzothiazole-2-amine is pramipexole or a pharmaceutically acceptable salt thereof, said dosage is equivalent to from 0.125 mg to 20 mg, from 0.125 mg to 15 mg, from 0.125 mg to 10 mg, from 0.125 mg to 7.5 mg or from 0.125 mg to 6 mg of pramipexole dihydrochloride monohydrate.

If 6-propylamino-4,5,6,7-tetrahydro-1,3-benzothiazole-2-amine is pramipexole dihydrochloride monohydrate, said dosage ranges from 0.125 mg to 20 mg, from 0.125 mg to 15 mg, from 0.125 mg to 10 mg, from 0.125 mg to 7.5 mg or from 0.125 mg to 6 mg.

Thus, according to a preferred embodiment the present invention provides a fixed-dose combination consisting of a pharmaceutical composition comprising (a) fluoxetine or a pharmaceutically acceptable salt thereof, in an amount per unit form equivalent to from 2 mg to 90 mg of fluoxetine base; and (b) pramipexole or a pharmaceutically acceptable salt thereof, in an amount per unit form equivalent to a range selected from the group consisting of from 0.125 mg to 20 mg, from 0.125 mg to 15 mg, from 0.125 mg to 10 mg, from 0.125 mg to 7.5 mg or from 0.125 mg to 6 mg of pramipexole dihydrochloride monohydrate, in admixture with a pharmaceutical carrier or vehicle.

The pharmaceutical compositions of the present invention are formulated with the classic excipients suitable for different ways of administration. Particularly advantageous are the formulations in the form of tablets, multi-score tablets, coated tables, orally disintegrating tablets, extended release tablets, hard or soft capsules, extended-release capsules, patches for transdermal administration, liquid oral solutions, syrups or suspensions in a predetermined unit form, and vials for the intravenous or subcutaneous administration.

Thus, for example, a pharmaceutical composition according to the present invention to be chronically administered in combination with 6-propylamino-4,5,6,7-tetrahydro-1,3-benzothiazole-2-amine, preferably pramipexole dihydrochloride monohydrate, in an amount/unit dose of from 0.125 mg to 20 mg, from 0.125 mg to 15 mg, from 0.125 mg to 10 mg, from 0.125 mg to 7.5 mg or from 0.125 mg to 6 mg to be administered at a daily dose of from 1.5 mg to 20 mg, from 1.5 mg to 15 mg, from 1.5 mg to 10 mg, from 1.5 mg to 7.5 mg, or from 1.5 mg to 6 mg, comprises fluoxetine hydrochloride, in an amount/unit dose (in fluoxetine) of from 2 mg to 90 mg to be administered at a daily dose of from 4 mg to 40 mg in IR or ER-form or at a weekly dose of 90 mg, in ER-form only.

The pharmaceutical compositions may be formulated in oral forms such as tablets or gelatin capsules, wherein fluoxetine or a pharmaceutically acceptable salt or solvate thereof; or the 6-propylamino-4,5,6,7-tetrahydro-1,3-benzothiazole-2-amine, preferably pramipexole or a pharmaceutically acceptable salt or solvate thereof; or both the active ingredients, are in admixture with a carrier or vehicle. Said carrier or vehicle may include a diluent, such as cellulose, dextrose, lactose, mannitol, sorbitol or sucrose; a lubricant, such as, acid, calcium or magnesium stearate, polyethylene glycol, silica, or talc; and if needed, a binder such as magnesium aluminum silicate, gelatin, methylcellulose, sodium carboxymethylcellulose, or polyvinylpyrrolidone.

Said oral forms may be tablets coated with sucrose or with various polymers.

Alternatively, the tablets can be manufactured by using carriers such as acrylic and methacrylic acid polymers and copolymers; cellulose derivatives such as hydroxypropylethylcellulose; or other appropriate materials. These materials confer a prolonged or delayed activity by progressively releasing a predetermined quantity of fluoxetine (or pharmaceutically acceptable salt thereof) or 6-propylamino-4,5,6,7-tetrahydro-1,3-benzothiazole-2-amine (or pharmaceutically acceptable salt or solvate thereof).

The oral formulations can also be in form of capsules allowing the extended release of fluoxetine (or a pharmaceutically acceptable salt or solvate thereof); of 6-propylamino-4,5,6,7-tetrahydro-1,3-benzothiazole-2-amine (or pharmaceutically acceptable salt or solvate thereof); or of both the active ingredients.

A fixed-dose combination according to the present invention may be a dosage unit form consisting of a capsule comprising for example fluoxetine hydrochloride Component (a), in an amount equivalent to 10 mg of fluoxetine base; and pramipexole dihydrochloride monohydrate Component (b), in an amount of 6.5 mg, in admixture with a pharmaceutical carrier.

Another fixed-dose combination may be formulated in tablets in which fluoxetine hydrochloride Component (a), in an amount equivalent to 10 mg of fluoxetine base is in an IR-formulation and pramipexole dihydrochloride monohydrate, in an amount of 7.5 mg, is in controlled-release formulation, for example as a dispersion of said component in hydroxypropyl methyl cellulose or in a film-coated microgranule. Said tablet may be a tablet with two superimposed layers, or a bilayer tablet wherein pramipexole dihydrochloride dihydrate, in ER-formulation is in the core and the fluoxetine, in IR-formulation, is in the outer layer. The core or both the core and the outer layer may coated with a film.

The pharmaceutical compositions may also be formulated in TTS, such as a patch formulation wherein the active ingredient or the mixture of the active ingredients may comprise adjuvants such as D-sorbitol, gelatin, kaolin, methyl paraben, polysorbate 80, propylene glycol, propyl paraben, povidone, sodium carboxymethylcellulose, sodium polyacrylate, tartaric acid, titanium dioxide, and purified water. A patch formulation may also contain skin permeability enhancer such as lactate esters (e.g., lauryl lactate), triacetin or diethylene glycol monomethyl or monoethylether.

In the above pharmaceutical compositions, the preferred fluoxetine, or a pharmaceutically acceptable salt or solvate thereof, active ingredient is fluoxetine base or its hydrochloride and the preferred 6-propylamino-4,5,6,7-tetrahydro-1, 3-benzothiazole-2-amine active ingredient, or a pharmaceutically acceptable salt thereof, is pramipexole base or its dihydrochloride monohydrate.

EXAMPLE 1

A Phase I-II clinical study was conducted in parkinsonian subjects receiving oral doses of pramipexole or fluoxetine, alone and in combination. The trial was designed as a single-blind, placebo-controlled study.

The objective of the study was to demonstrate that pramipexole and fluoxetine, when administered together at their standard therapeutic doses, can safely normalize concentrations of synuclein species in peripheral blood exosomes.

To be enrolled in the study, male or female participants (40 to 89 years of age) were required to carry the diagnosis of Parkinson's disease or a related synucleinopathic disorder. Additionally, they had to agree to refrain from other anti-parkinsonian (excepting levodopa-carbidopa) or antidepressant drugs, and to avoid prolonged intensive physical exercise during the conduct of this study. All subjects signed an informed consent form indicating that they understood the purpose of and procedures required for the study and that they were willing to participate in the study and comply with all study procedures and restrictions. Key criteria for exclusion of a subject from enrollment in the study were as follows:
1. Any clinically relevant acute or chronic disease which could interfere with the subjects' safety during the trial, expose them to undue risk, or interfere with the study objectives.
2. History or presence of gastrointestinal, hepatic, or renal disease or other condition known to interfere with the absorption, distribution, metabolism or excretion of the study medications;
3. History of substance abuse, known drug addiction, or positive test for drugs of abuse or alcohol.
4. History of drug or other significant allergy.
5. Congenital long QT syndrome; a previous history of QT prolongation; a family history of long QT syndrome or sudden cardiac death; and other conditions that predispose to QT prolongation and ventricular arrhythmia
6. Treatment with centrally active drugs except for levodopa-carbidopa given at a stable dose for at least 3 months.
7. Excessive daily consumption of xanthines containing drinks (i.e. >500 mg/day of caffeine).
8. Hospitalization or intake of an investigational drug within 30 days of study entry.

Following baseline clinical and laboratory evaluations, consenting individuals meeting accession criteria were first randomized to either pramipexole or fluoxetine treatment. In either case, dosage of the initial drug was gradually increased over the ensuing 6-8 weeks in accordance with current recommendations to each patient's maximum tolerated dose (MTD) or the maximum recommended dose, whichever is lower, and stably maintained for approximately 6 weeks. Patients then entered the next study phase, lasting about 6-8 weeks when the second study medication was added to their ongoing treatment regimen, in accordance with its recommended titration schedules to their MTD or the maximum recommended dose. Once safe and tolerable doses of the drug combination were achieved, it was stably maintained for approximately 6 weeks. Doses of both drugs were then be tapered in accordance with current recommendations and patients were returned to their pre-admission regimen pending discharge from the study.

Drug safety-tolerability was monitored by means of standard clinical and laboratory tests on a weekly basis during dose titration, and otherwise at intervals not exceeding every 4 weeks. Weekly telephone interviews were generally conducted on those not scheduled for a clinic visit. A final safety check was performed approximately one month after withdrawal of all study medications.

Additionally, venous blood for synuclein and drug assays was collected on the same schedule.

Results surprisingly showed that the oral administration of a combination of pramipexole and fluoxetine was associated with characteristic alterations in synuclein and synuclein congener concentrations in exosomes collected from peripheral venous blood samples from patients who safely tolerated their therapeutic regimens.

In conclusion, the co-administration of standard approved doses of pramipexole and fluoxetine yielded clear peripheral evidence of a drug-combination-induced tendency to normalize synuclein processing indicative of a reduction in toxic species formation in the central nervous system of a type associated with a neuroprotective efficacy that clinically benefits patients suffering from Parkinson's disease or a related synucleinopathy.

REFERENCES

Al-Mansoori et al. 2013: Al-Mansoori KM, Hasan MY, Al-Hayani A, El-Agnaf M, "*The role of α-synuclein in neurodegenerative diseases: from molecular pathways in disease to therapeutic approaches*"; Curr. Alzheimer Res. 2013 July; 10(6): 559-568.
Bymaster et al. 2002: Bymaster F, Zhang W, Carter P, Shaw J, Chernet E,; Phebus L, Wong D, PerryK;. "*Fluoxetine, but not other selective serotonin uptake inhibitors, increases norepinephrine and dopamine extracellular levels in prefrontal cortex via serotonin type 2C antagonism.*"; Psychopharmacology 2002160(4): 353-61
Chen et al. 2016: Chen M, Weiwei Yang W, Li Xin, X, Li Xuran, Wang P, Feng Yue F, Yang H, Chan P, and Yu S; "*Age- and brain region-dependent α-synuclein oligomerization is attributed to alterations in intrinsic enzymes regulating α-synuclein phosphorylation in aging monkey brains*"; Oncotarget. 2016 Feb. 23; 7(8): 8466-8480.
Chung et al, 2011: Neuropharmacology, Volume 60, Issue 6, May 2011, Pages 963-974.
Corrigan et al. 2000: Corrigan M H, Denahan A Q, Wright C E, Ragual R J, Evans D L; Corrigan M H, Denahan A Q, Wright C E, Ragual R J, Evans D; "*Comparison of pramipexole, fluoxetine, and placebo in patients with major depression*"; Depress Anxiety. 2000;11(2):58-65.
Inden et al. 2009: Inden M, Kitamura Y, Tamaki A, Yanagida T, Shibaike T, Yamamoto A, Takata K, Yasui H, Taira T, Ariga H, Taniguchi T; "*Neuroprotective effect of the antiparkinsonian drug pramipexole against nigrostriatal dopaminergic degeneration in rotenone-treated mice.*"; Neurochem Int. 2009 December; 55(8):760-7.
Jellinger K A 2008a: Jellinger K A, "*A critical reappraisal of current staging of Lewy-related pathology in human brain*"; Acta Neuropathol. 2008 July; 116(1): 1-16.
Jellinger K A 2008b: Jellinger K A, "*Neuropathological aspects of Alzheimer disease, Parkinson disease and frontotemporal dementia*"; Neurodegener. Dis. 2008; 5(3-4): 118-121
Kakimura et al. 2001: Kakimura J, Kitamura Y, Takata K, Kohno Y, Nomura Y, Taniguchi T; "*Release and aggre-* gation of cytochrome c and alpha-synuclein are inhibited by the antiparkinsonian drugs, talipexole and pramipexole"; Eur J Pharmacol. 2001 Apr. 6;417(1-2):59-67.

Kim et al. 2004: Kim S, Seo J H, Suh Y H, "*Alpha-synuclein, Parkinson's disease, and Alzheimer's disease*"; Parkinsonism Relat. Disord. 2004 May; 10 Suppl. 1: S9-13.

Luo et al. 2016: Luo H T, Zhang J P, Miao F; "*Effects of pramipexole treatment on the α-synuclein content in serum exosomes of Parkinson's disease patients*"; ExpTher Med. 2016 September;12(3):1373-1376.

Marques and Outeiro 2012: Marques 0, Outeiro T F; "*Alpha-synuclein: from secretion to dysfunction and death*"; Cell Death Dis. 2012 Jul. 19;3:e350. doi: 10.1038/cddis.2012.94.

Ono et al. 2013: Ono K, Takasaki J, Takahashi R, Ikeda T, Yamada M; "*Effects of antiparkinsonian agents on β-amyloid and α-synuclein oligomer formation in vitro*";JNeurosci Res; 2013 October ;91(10):1371-81).

O'Regan et al 2017: O'Regan G, DeSouza R M, Balestrino R, "Glucocerebrosidase Mutations in Parkinson Disease" J Parkinson's Dis 7 (2017) 411-422-DOI 10.3233/JPD-171092.

Prusiner SB et al. 2015:Prusiner S B[1], Woerman A L[2], Mordes D A[3], Watts J C[4], Rampersaud R[2], Berry D B[2], Patel S[2], Oehler A[5], Lowe J K[6], Kravitz S N[6], Geschwind D H[7], Glidden D V[8], Halliday G M[9], Middleton L T[10], Gentleman S M[11], Grinberg L T[12], Giles K[4], "*Evidence for α-synuclein prions causing multiple system atrophy in humans with parkinsonism*" ProcNatlAcadSci U S A; 2015, Sep. 22;112(38):E5308-17.

Schapira et al. 2013: Schapira A H, McDermott M P, Barone P, Comella C L, Albrecht S, Hsu H H, Massey D H, Mizuno Y, Poewe W, Rascol O, Marek K. "Pramipexole in patients with early Parkinson's disease (PROUD): a randomised delayed-start trial"; Lancet Neurol. 2013 August;12(8):747-55).

Schneider C S and Mierau J, 1987: Schneider C S, Mierau J "Dopamine autoreceptor agonists: resolution and pharmacological activity of 2,6-diaminotetrahydrobenzothiazole and an aminothiazole analogue of apomorphine"; J. Med Chem. 1987 March;30(3):494-8.

Shi et al. 2014: Shi M, Liu C, Cook T J, Bullock K M, Zhao Y, Ginghina C, Li Y, Aro P, Dator R, He C, Hipp M J, Zabetian C P, Peskind E R, Hu S C, Quinn J F, Galasko D R, Banks W A, Zhang J; "*Plasma exosomal α-synuclein is likely CNS-derived and increased in Parkinson's disease*";ActaNeuropathol. 2014 November;128(5):639-50. doi: 10.1007/s00401-014-1314-y. Epub 2014 Jul. 6.

Shults et al. 2005: Shults C W, Rockenstein E, Crews L, Adame A, Mante M, Larrea G, Hashimoto M, Song D, Iwatsubo T, Tsuboi K, Masliah E.; "*Neurological and neurodegenerative alterations in a transgenic mouse model expressing human alpha-synuclein under oligodendrocyte promoter: implications for multiple system atrophy*"; J Neurosci 2005, Nov. 16;25(46):10689-99.

Soria et al 2017: Soria F N, Engeln M, Martinez-Vicente M, Glangetas C, Lopez-Gonzales J, Dovero S, Dehay B, Normand E, Vila M, Lopez-Gonzales M J, Favereaux A, Georges F, Lo Bianco C, Bezard E, Fernagut; "Glucocerebrosidase deficiency in dopaminergic neurons induces microglial activation without neurodegeneration"; Hum Mol Genet 2017 July;26(14):2603-2615.

Stuendl et al. 2016: Stuendl A, Kunadt M, Kruse N, Bartels C, Moebius W, Danzer K M, Mollenhauer B, Schneider A; "*Induction of alpha-synuclein in aggregate formation by CSF exosomes from patients with Parkinson's disease and dementia with Lewy bodies*" Brain 2016, 139; 481-494

Suzuki et al. 2010: PLoS One. 2010 Feb. 17;5(2):e9260. doi: 10.1371/journal.pone.0009260.

Ubhi et al. 2012: Ubhi K, Inglis C, Mante M, Patrick C, Adame A, Spencer B, Rockenstein E, May V, Winkler J, Masliah; "*Fluoxetine ameliorates behavioral and neuropathological deficits in a transgenic model mouse of α-synucleinopathy*"; E. Exp Neurol. 2012 April;234(2): 405-16.

Visanji N P et al 2016: Visanji N P, Brotchie J M, Kalia L V, Koprich J B, Tandon A, Watts J C, Lang A E ; "α-*Synuclein-Based Animal Models of Parkinson's Disease: Challenges and Opportunities in a New Era*"; Trends Neurosci. 2016 November;39(11):750-762.

The invention claimed is:

1. A method for treating a patient suffering from a synucleinopathy which comprises treating said patient with fluoxetine or a pharmaceutically acceptable salt or solvate thereof in combination with a 6-propylamino-4,5,6,7-tetrahydro-1,3-benzothiazole-2-amine or of a pharmaceutically acceptable salt or solvate thereof.

2. The method of claim 1 wherein said synucleinopathy is selected from the group consisting of Parkinson's disease, Lewy body disease, Alzheimer's disease, mutations in the glucocerebrosidase gene, and multiple system atrophy.

3. The method of claim 1, wherein said 6-propylamino-4,5,6,7-tetrahydro-1,3-benzothiazole-2-amine or pharmaceutically acceptable salt or solvate thereof is (S)-6-propylamino-4,5,6,7-tetrahydro-1,3-benzothiazole-2-amine dihydrochloride monohydrate.

4. The method of claim 1, wherein said fluoxetine is formulated in a pharmaceutical composition in dosage unit form comprising said fluoxetine in an amount per unit form of from 2 mg to 90 mg and said 6-propylamino-4,5,6,7-tetrahydro-1,3-benzothiazole-2-amine is formulated in a pharmaceutical composition in dosage unit form comprising said 6-propylamino-4,5,6,7-tetrahydro-1,3-benzothiazole-2-amine in an amount equivalent to from 0.125 mg to 3000 mg of pramipexole dihydrochloride monohydrate, said amount including a (S)-enantiomer amount equivalent to from 0.125 mg to 20 mg of pramipexole dihydrochloride monohydrate.

5. The method of claim 4, wherein said fluoxetine or pharmaceutically acceptable salt thereof is formulated in a pharmaceutical composition in dosage unit form comprising said fluoxetine or pharmaceutically acceptable salt thereof in an amount per unit form of from 2 mg to 40 mg in an IR- or ER-formulation.

6. The method of claim 4, wherein said fluoxetine or pharmaceutically acceptable salt thereof is formulated in a pharmaceutical composition in dosage unit form comprising said fluoxetine or pharmaceutically acceptable salt thereof in an amount per unit form of 90 mg in an ER-formulation to be administered once a week.

7. The method of claim 4, wherein said fluoxetine or pharmaceutically acceptable salt thereof is administered at a daily dose equivalent to from 4 mg to 40 mg of fluoxetine base and said 6-propylamino-4,5,6,7-tetrahydro-1,3-benzothiazole-2-amine or of a pharmaceutically acceptable salt or solvate thereof is administered at a daily dose equivalent to from 1.5 mg to 3000 mg of pramipexole dihydrochloride monohydrate, said daily dose including a (S)-enantiomer daily dose equivalent to from 1.5 mg to 6 mg of pramipexole dihydrochloride monohydrate.

* * * * *